United States Patent [19]

Boettger et al.

[11] Patent Number: 4,793,185
[45] Date of Patent: Dec. 27, 1988

[54] NONDESTRUCTIVE TESTING

[75] Inventors: Wolfgang Boettger, Duesseldorf; Willi Weingarten, Moers; Heinz Schneider, Duesseldorf, all of Fed. Rep. of Germany

[73] Assignee: Mannesmann AG, Duesseldorf, Fed. Rep. of Germany

[21] Appl. No.: 39,672

[22] Filed: Apr. 17, 1987

[30] Foreign Application Priority Data

Apr. 24, 1986 [DE] Fed. Rep. of Germany ....... 3614069

[51] Int. Cl.$^4$ ............................................ G01N 28/04
[52] U.S. Cl. .................................................... 73/643
[58] Field of Search .......................... 73/622, 643, 644

[56] References Cited

U.S. PATENT DOCUMENTS 4,312,231  1/1982  Kawashima et al. ................. 73/643
4,596,147  6/1986  Behl et al. ............................ 73/643
4,602,512  7/1986  Kowol et al. ......................... 73/643

Primary Examiner—Stewart J. Levy
Assistant Examiner—Louis M. Arana
Attorney, Agent, or Firm—Ralf H. Siegemund

[57] ABSTRACT

Electrically conductive work pieces such as steel tubes or pipes are tested by means of a transducer comprised of a row of magnetic pole pieces through which a dc flux pattern of alternating polarity and direction is set up along a line of pole extensions and through which bidirectional ac ultrasonic transmission takes place to discover defects which return ultrasonic pulses.

11 Claims, 3 Drawing Sheets

NONDESTRUCTIVE TESTING

BACKGROUND OF THE INVENTION

The present invention relates to the nondestructive testing of structural materials, work pieces, components or the like made of an electrically conductive material whereby the test includes passing a movable electromagnetic system across the piece to be tested which system is comprised of at least one pole piece being surrounded by a magnetizing coil and being on one side connected to a soft magnetic (high permeability with little or no hysteresis) return path. Moreover, the equipment is assumed to provide for ultrasonic transmission and receiving.

Electrodynamic ultrasonic transducers are known and have been described extensively in the literature as to both their structure as well as to their function. A significant number of papers has been devoted to analysis and description of such transducers. Basically they are comprised in each instance of a transmission coil and of a receiver coil or of a combined time sharing transmission/receiving coil. They are arranged in a static electromagnetic field and particularly physical relation to the piece to be tested and here particularly close to the surface thereof. Upon electrically energizing the transducer (transmitter or transmitting) coil an ultrasonic pulse is produced in the work piece. Either the same coil or the receiving coil will receive any response by the work piece such as an echo and produces an electrical pulse (physical movement in the static magnetic field) having a particular temporal amplitude possibly also frequency relation to the initial pulse.

All these ultrasonic transducers as described are to be used on planar as well as curved work pieces for purpose of nondestructive testing; there is no basic limitation involved. As an example see e.g. European Pat. No. 24 707. This equipment, however, exhibits a certain restriction in that preferably only one or two coils at the most can be used. This limitation results from the fact that the conversion of ultrasonic into electromagnetic energy and vice versa requires a relatively high static magnetic fields, and for this reason only a limited amount of space is available for effective transduction unless special steps are taken for limiting e.g. any spreading effect of that field. In order to improve and enlarge the testing power and capability, i.e. in order to speed up the overall testing process it has been suggested to provide a plurality of such ultrasonic transducers and in a rather close spacial relationship. Also they are associated with a common static magnetic field. In order to avoid interference these transducers are controlled to operate in a certain sequence under utilization of suitably programmed electronic circuit. In other words, one uses the high speed operation of the transducer and pulse transmission, propagation and receiving to bridge the relatively slow movement between transducer and workpiece to be tested.

Also known is a transmitter arrangement (see German printed patent application No. 28 45 579) wherein the transmitter is associated with one pole and several receiver coils are associated with the same or the other piece. The test speed attainable with such a device is still not regarded as sufficient since the test speed is limited by the size of the magnet even if one uses more and more transducer coils or coil pairs within a homogenic magnetic field.

DESCRIPTION OF THE INVENTION

It is an object of the present invention to provide a new and improved eletrodynamically operating ultrasonic transducer to be used in non-destructive testing of structural materials with the goal in mind to increase the test speed to insure gapless scanning of the work piece and to improve guidance and movement of the transducer across the work piece surface in a rather simple manner.

In accordance with the preferred embodiment of the present invention, the object is attained by providing an electromagnet for purposes of generating a homogeneous static magnetic field. This electromagnet is to be of plural pole construction i.e. it is of a comb-like configuration whereby the polarity alters from pole to pole. The linearity facilitates the electromagnetic interaction with the work piece. The gaps between the pieces are filled with coils passed through by and energized by a d.c. current. Transducer coils proper are also arranged (or stored) on the plural pole magnets to obtain bidirectional electromagnetic ultrasonic interaction between the transducers and the work piece. If defects are present in the work piece adjacent to any pole pieces the reflection produced by such a defect induces a voltage in the receiving coil which then is indicated.

The comb-like configured electrodynamic ultrasonic transducer will be guided across the surface of the workpiece in the direction of motion which is perpendicular to the extension of the row of poles in the transducer. In the case of tubes or pipes to be tested the entire volume of the tube wall can be tested by a helical motion of the tube. The electrodynamic transducer remains stationary in this case the "prongs" of the comb being arranged parallel to the axis of the tube. This particular approach is deemed more advantageous than any attempt to widen the magnetic flux path pattern of a magnetic pole.

A preferred embodiment of the invention provides a uniformization of the magnetic flux for each of the pole by narrowing the pole piece in a plane transverse to the row extension of the pole pieces. A futher particular feature is the provision of caps on the pole pieces for receiving the transducer coils with plugs being provided for plugging in all of the coils simultaneously. Moreover, the spacing of the transducer coils as well as the pole pieces should be matched to compensate for any surface unevenness of the workpiece. The caps particularly permits matching the effective free end surface of the pole pieces to the geometric contour of the work piece; for example a typical work piece to be tested is a tube or a pipe. The cap's contour facing the work piece should be concavely curved to match the convex contour of the tube or pipe. The caps for the pole pieces should be constructed in a wearproof fashion. Another feature for equalizing the magnetic conditions in the test are to be seen in providing an additional pole piece without transduction in front as well as of the rear of the row.

In the case of helical testing i.e. being last in continuous testing of a thick pipe respective two adjacent pole pieces of different magnetic flux should be separated by a chamber being flown through by a coolant. This is necessary since helical testing of a tube or pipe is a continuous and fairly long lasting operation.

DESCRIPTION OF THE DRAWINGS

While the specification concludes with claims particularly pointing out and distinctly claiming the subject matter which is regarded as the invention, it is believed that the invention, the objects and features of the invention and further objcts, features and advantages thereof will be better understood from the following description taken in connection with the accompanying drawings in which:

Proceeding now to the detailed description of the drawings FIG. 1 and 2 illustrate a tube or pipe 8 to be tested. At a very small distance (or no distance at all) there is provided an ultrasonic transducer operated by means of electrodynamics and having pole pieces 1–7 arranged in a row that extends along and parallel to the axis of the tube. The distance and spacing of adjacent ones of pole pieces 1–7, as can be seen in FIG. 1, is equal to the thickness of the pole piece in the direction of row extension. This spacing is filled with coils 10–16 respectively surrounding the pole pieces 1–7. The coils are oriented and wound and flown through a magnetizing current such that the polarity of the downwardly oriented free ends of the pole pieces 1–7 alternate. The respective other ends of the pole pieces 1–7 are all interconnected by means of a common return path yoke 17.

Figure 1:
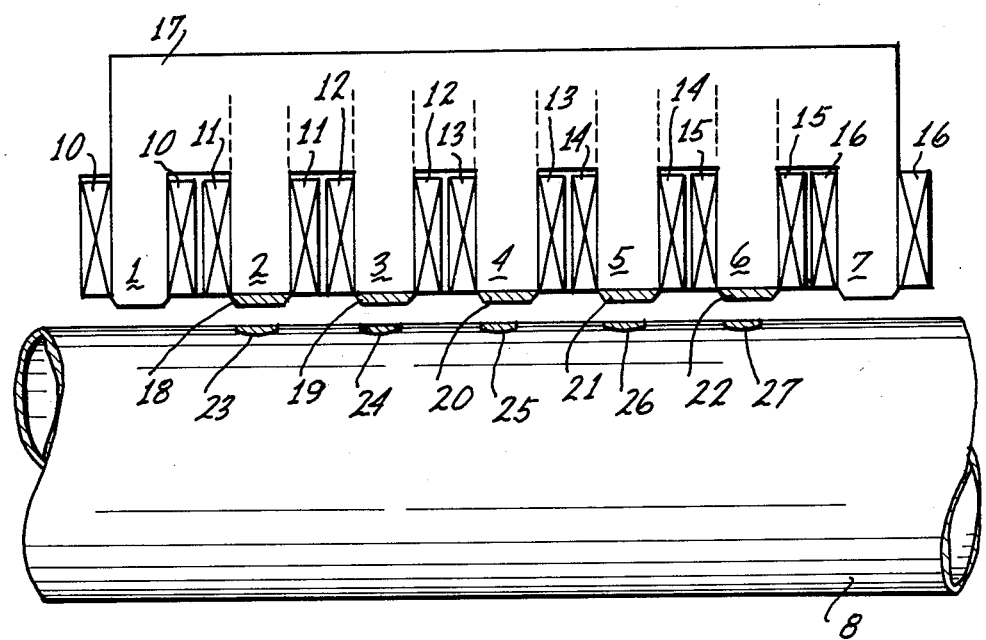
FIG. 1 is a schematic section through an electrodynamic ultrasonic transducer constructed in accordance with the preferred embodiment of the present invention for practicing the best mode thereof in conjunction with the testing of tubes or pipes.

The four pieces or core elements 2, 4, 5 and 6 carry on their free ends caps 18, 19, 21, 22 respectively. These caps are embedded in those respective coils which will receive energizing electric current pulses so that on the basis of the homogeneous static magnetic flux ultrasonic waves will be produced in the cross hatch areas 23–27 into which all are embedded and will receive a current pulse. After each pulse, ultrasonic reflection waves of any defects will be received as they emerge from the tube 8. The transducer receiving them converts them into electrical pulses. These pulses trigger in other parts of the device i.e. in an appropriate circuit (not shown) indication of errors or devices are for recording or for marking the location of a defect marking on the surface of the tube. The pole pieces 1–7 are symmetrical and in order to provide a highly homogeneous field of uniform strength no transductor coils are provided on the pole pieces 2 and 7, only a coil for generating the static magnetic field.

The coils 10–16 also designated to be coil means could in each instance be one of the following: (i) three coils, one of which is flown through by dc to establish the basic magnetization pattern including the alternations of polarity at the ends of the cores or pieces 1–7. A second coil receives a current pulse which by way of electromagnetic interaction sets up ultrasonic vibrations. A third coil responds to variations in the magnetic field on account of physical movements in the pipes' material resulting from ultrasonic agitation attributable to an echo or a defect in the tube's material. (ii) The function of the second and third coil can be combined in a single coil operated by way of electronic control on a time sharing basis; it is used as transmitter coil upon application of an electric energizing pulse but is separated from that source of magnetizing pulses shortly thereafter and reconnected to a receiving circuit by way of signal gating to become responsive to variations in the magnetic field attributable to a return echo. (iii) Through filtering a single coil can be used which applies the dc energization of a dc circuit, and through ac coupling trigger pulses can be superimposed, and low pass or bandpass filtering can sort out from the signals in the circuit those signals that can be attributable to a return pulse.

In furtherance of the invention, the coil means 10 and 16 should be provided only for dc energization and not participate in ac transduction i.e. the pole pieces 1 and 7 will not be operated for transmission of magnetic pulses nor for receiving alterations in the local magnetic field on account of echo induced local movement.

The main direction of testing progresses in a direction transversely to the plane of the drawing. This obtains through rotation and axial advance of the tube 8. The electrodynamic transducer is stationarily mounted in a frame so that upon rotational movement of the tube 8 every portion of that tube passes under the transducers. In fact the tube may slidingly abut the caps 18–22.

Complete volume testing of the entire tube wall is carried out through two sets of such multiple pole pieces electromagnetic transducers 27 and 28. Both exhibit a row of poles. These transducers are arranged shifted in relation to each other by half a pole to pole spacing to obtain a staggered arrangement of transducers. They are moreover arranged in the direction of testing shown in FIG. 2. The main direction of test movement is indicated by arrow 30 in FIG. 2. For matching the rows of electromagnetic transducers in the transducers 27 and 28 the different diameters are interconnected by means of hinges 29 and 29'. The electrical connections are not shown in this figure.

Figure 2:
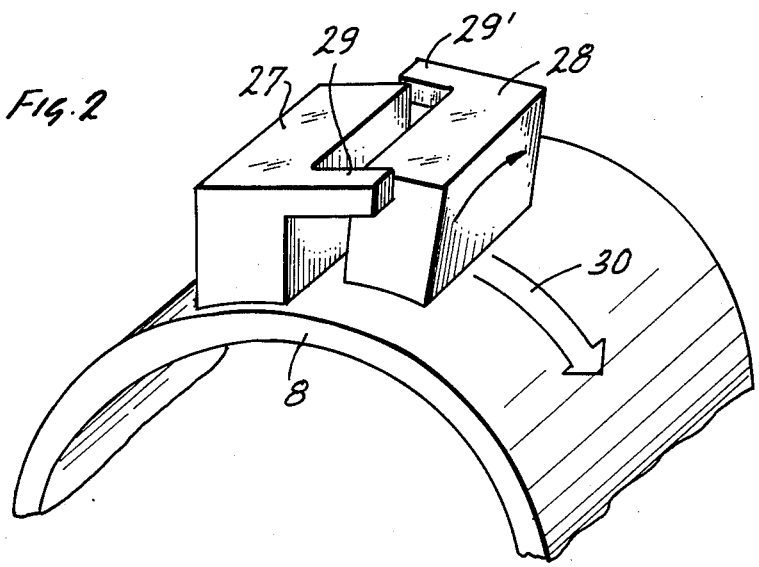
FIG. 2 is an isometric-perspective view of a twin arrangement using two apparatuses for full volume testing of the wall of tubes in one particular passage.
Figure 3:
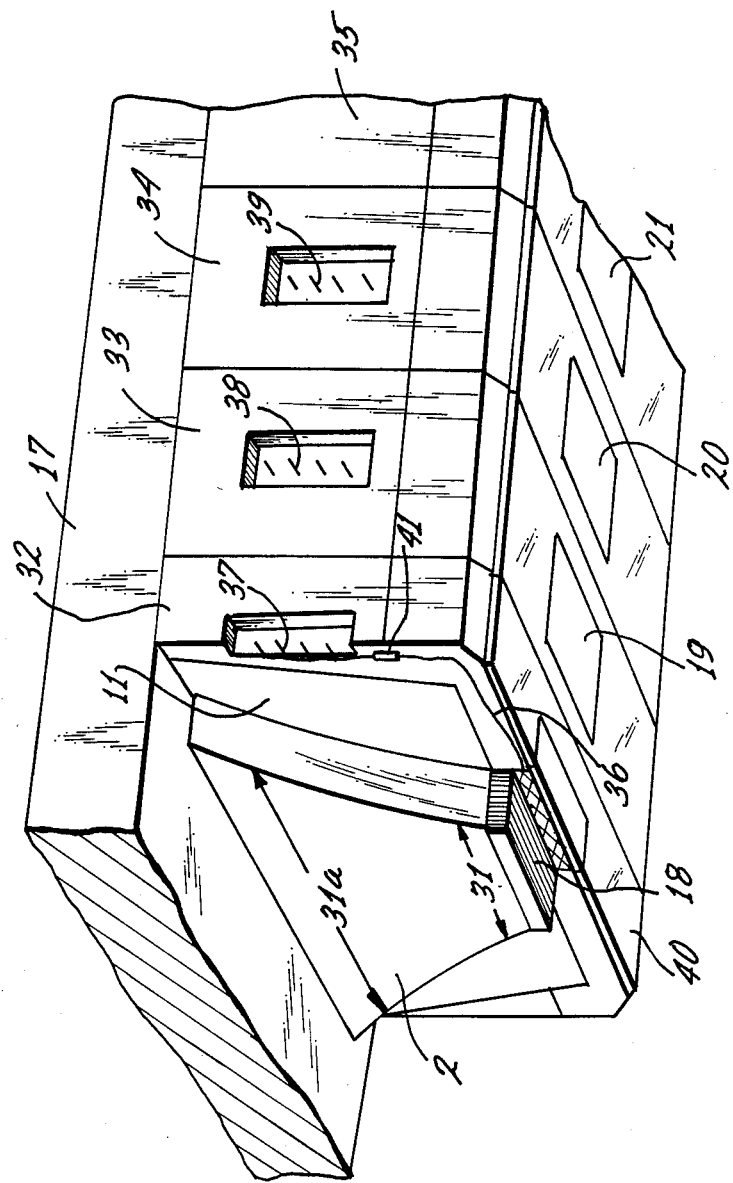
FIG. 3 is an isometric perspective view of an equipment used in the embodiment and example of FIG. 1 with a cut away portion.

FIG. 3 uses the same designations and parts designated by similar reference numerals as shown in reference to FIGS. 1 and 2. In addition however this figure shows the width 31 and 31a of one of the poles such as 2. This figure demonstrates that in order to obtain a highly uniform magnetic flux and field one provides a width 31 at the free pole ends so that the gap is smaller than near or right in the magnetic return path 17. Here the gap is denoted by reference numeral 31a. The tapered configuration of the pole pieces is selected such that during operation the magnetization of the core comes close to but does not reach saturation throughout the entire extension of the core or pole pieces.

Figure 4:
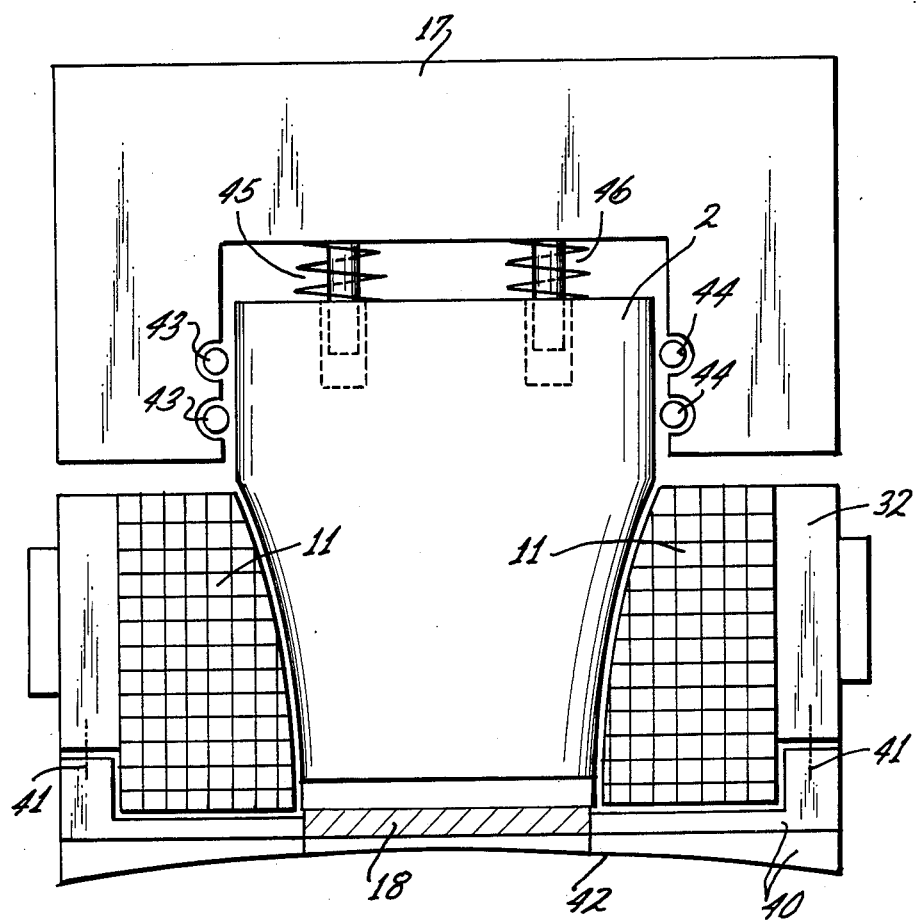
FIG. 4 is a view showing particularly an adjustable pole piece.

The coil 11, the pole piece 2 itself etc. are provided with linings 32–35 respectively under which conductor 36 have been installed leading to plug connection 37, 38 and 39. The front parts of the linings 32–35 are actually provided as supplement caps 40 in which the coils such as 18 are embedded as plug connections 41 for the coil are also embedded in that supplemental cap. Moreover the supplemental caps 40 may be provided with wearproofing and lining. As shown in FIG. 4, the lower ends of the caps do not have to be straight but are concavely shaped to match the curved surface of the tubes to be tested.

FIG. 4 illustrates a conceivable modification for the pole pieces such as 2 using otherwise the same designation as previously used. The pole piece 2 is mounted by means of needle bearings 43 and 44 inside the return path yoke 17'. This way the pole piece 2 can be moved towards and away from the work piece together with the coils 11 it carries as well as the cap 40. This feature permits adjustment of the equipment vis-a-vis the tube to be tested. The apparatus is under tension of springs 45 and 46; these springs provide a pressure of the test equipment against the tube to be tested to make sure that there is always present full and complete coupling of the transducer to the work piece itself.

The invention is not limited to the embodiments described above but all changes and modifications thereof, not constituting departures from the spirit and scope of the invention, are intended to be included.

We claim:

1. Electromagnetic transducer for nondestructive testing of structural, electrically conductive material comprising:
   a plurality of pole pieces arranged in a row, each of the pole pieces having a free end facing the piece to be tested;
   a soft magnetic return path and flux member connected to the respective opposite ends of all of the pole pieces; and
   a plurality of transducer coil means arranged on these pole pieces and provided for dc energizing such that the magnetic polarity at the free ends of the pole pieces alternate along the row, further provided for generating magnetically ultrasonic signal producing pulses, and for responding to magnetic field variations on account of ultrasonic echos.

2. Transducer as in claim 1 wherein the number of transducer coil means corresponds to the number of pole pieces or to the number of gaps between the pole pieces.

3. Transducer as in claim 1 the pole pieces have at their free end at least approximately a square shaped cross section, the respective side of the square is equal to a gap spacing in between two adjacent pole pieces.

4. Transducer as in claim 1 wherein the width of the pole pieces increases, from the respective free end, towards the magnetic return flux the width being taken transversely to the direction of row extension, and that in all cross sections in any distance from the free end of the respective pole piece, magnetic saturation does not obtain.

5. Transducer as in claim 1 wherein said pole pieces are mounted for relative movement in relation to the return path flux member, there being spring means for urging the pole pieces towards and onto the workpiece to be tested.

6. Transducer as in claim 1 said free ends of the pole pieces have a surface contour matching the surface of the object to be tested.

7. Transducer as in claim 1 said free ends of the pole pieces being concavely shaped.

8. Transducer as in claim 1 at least some of the pole pieces carry workpiece matching caps; the caps where facing the workpiece being provided with a wear-proofing.

9. Transducer as in claim 8 said coils being embedded in the caps.

10. Transducer as in claim 1 including chamber means in between adjacent pole pieces being flown through by a coolant.

11. Transducer as in claim 1 and including two rows of pole pieces running parallel and being arranged in a staggered relationship.

* * * * *